United States Patent [19]

Wu et al.

[11] Patent Number: 5,594,000
[45] Date of Patent: Jan. 14, 1997

[54] SPIROFURANE DERIVATIVES

[75] Inventors: Edwin S.-C. Wu, Rochester; Ronald C. Griffith, Pittsford, both of N.Y.

[73] Assignee: Astra AB, Södertälje, Sweden

[21] Appl. No.: 469,791

[22] Filed: Jun. 6, 1995

Related U.S. Application Data

[63] Continuation of Ser. No. 304,422, Sep. 12, 1994, abandoned, which is a continuation of Ser. No. 28,681, Mar. 8, 1993, abandoned, which is a continuation of Ser. No. 629,797, filed as PCT/US90/03351, Jun. 20, 1990, abandoned, which is a continuation-in-part of Ser. No. 369,324, Jun. 21, 1989, Pat. No. 5,075,317.

[51] Int. Cl.$^6$ .................. C07D 471/10; C07D 405/06; C07D 211/44; A61K 31/445
[52] U.S. Cl. .................. 514/278; 546/16; 546/207; 546/242
[58] Field of Search ................. 514/278; 546/16

[56] References Cited

U.S. PATENT DOCUMENTS

| 4,735,944 | 4/1988 | Bollinger | 546/19 |
| 4,940,795 | 7/1990 | Tsukamoto | 514/278 |

FOREIGN PATENT DOCUMENTS

| 0293093 | 3/1987 | European Pat. Off. |
| 0291673 | 3/1988 | European Pat. Off. |
| 311313  | 4/1989 | European Pat. Off. |

OTHER PUBLICATIONS

Takemura et al., Chem. Pharm. Bull. 29, 10, 3019–3025 (1981), "Synthesis and Selective Activity of Cholinergic Agents with Rigid Skeletons".
Coldham et al., Tet. Letters, 29, 41, 5321 (1988), "Stereochemically Control Synthesis of Spirocyclic Lactones and Ethers from N–methyl–4–piperidone and 3–quinuclidinone by Phenylthio Migration".
Shapiro et al., Chem. Ab., 90:20383K, "Synthesis of Nitroxyl Radicals Based on 4–ethyl–4–hydroxy–2,2,6,6–tetramethylpiperidine." (1979).
Azerbaev et al., Chem Abs. 74:111879r "Synthesis of 1,2, 5–trimethyl–4–(3–hydroxy–1–propynyl)–4–piperidinol and Its Reactions." (1971).
Azerbaev et al., Chem. Abs. 70:96659r, "Synthesis and Reactions of 2,5–dimethyl–4–(3–methyl–3–hydroxy–1–butynyl)–4–piperidinol." (1968).
Aggleton, J. P., Blindt, H. S., and Candy, J. M. (1989). Working memory in aged rats. *Behavioral Neuroscience*, 103(5):975–983.
Bartus, R. T., Dean, R. L., and Beer, B. (1980). Memory deficits in aged cebus monkeys and facilitation with central cholinomimetics. *Neurobiology of Aging*, 1:145–152.
Bartus, R. T. (1985). The cholinergic hypothesis: a historical overview, current perspective, and future directions In: D. S. Olton, E. Gamzu, S. Corkin (Eds.), *Memory dysfunctions an integration of animal and human research from preclinical and clinical perspectives*, New York: Annals of the New York Academy of Sciences, vol. 444: 332–358.

Becker, R. E. (1991). Therapy of the cognitive deficit in Alzheimer's disease: the cholinergic system. In: R. E. Becker, E. Giacobini (Eds.), *Cholinergic basis for Alzheimer therapy*, Boston: Birkhauser, 1–22.
Bonner, T. I. (1989). New subtypes of muscarinic acetylcholine receptors. *Trends in Pharmacological Sciences*, suppl., 11–15.
Christie, J. E., Shering, A., Ferguson, J., and Glen, A. I. M. (1981). Physostigmine and arecoline: effects of intravenous infusions in Alzheimer presenile dementia. *British Journal of Psychiatry*, 138:46–50.
Davis, K. L., Thal, L. J., Gamzu, E. R., Davis, C. S., Woolson, R. F., Gracon, S. I., Drachman, D. A., Schneider, D. A. Schneider, L. S., Whitehouse, P. J., Hoover, T. M. Morris, J. C., Kawas, C. H. Knopman, D. S., Earl, N. L., Kumar, V., and Doody, R. S. (1992). A double–blind, placebo–controlled multicenter study of tacrine for Alzheimer's disease. *The New England Journal of Medicine*, 327(18):1253–1259.

(List continued on next page.)

*Primary Examiner*—Mark L. Berch
*Attorney, Agent, or Firm*—McAulay Fisher Nissen Goldberg & Kiel, LLP

[57] ABSTRACT

Compounds of general formula I,

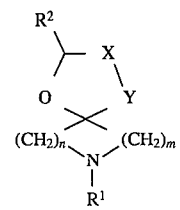

wherein $R^1$ represents hydrogen or alkyl $C_{1-3}$, $R^2$ represents hydrogen, alkyl $C_{1-6}$, alkenyl $C_{3-6}$ or alkynyl $C_{3-6}$, n and m are integers from 1 to 3, provided that n+m=4, and one of X and Y represents $CH_2$ and the other represents $CHR^3$, $C=CHR^4$ or $C=NR^5$, in which $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined in the specification, and their salts are useful as pharmaceuticals, in particular as central muscarinic acetylcholine receptors. The compounds are therefore useful in the treatment of diseases such as presenile and senile dementia, Huntington's chorea, tardive dyskinesia, hyperkinesia, mania and Tourette Syndrome, and also as analgesic agents for use in the treatment of severe painful conditions such as rheumatism, arthritis, and terminal illness.

9 Claims, No Drawings

OTHER PUBLICATIONS

Eagger, S. A., Levy, R., and Sahakian, B. J. (1991). Tacrine in Alzheimer's disease. *The Lancet*, 337:989–992.

Farlow, M., Gracon, S. I., Hershey, L. A., Lewis, K. W., Sadowsky, C. H., and Dolan–Ureno, J. (1992). A controlled trial of tacrine in Alzheimer's disease. *Journal of the American Medical Association*, 268(18):2523–2529.

Goyal, R. K. (1989). Muscarinic receptor subtypes: physiological and clinical implications. *The New England Journal of Medicine*, 321(15):1022–1029.

Katzman, R. (1986). Medical progress: Alzheimer's disease. *The New England Journal of Medicine*, 314(15):964–973.

Messer, W. S., Bohnett, M., and Stibbe, J. (1990). Evidence for a preferential involvement of M1 muscarinic receptors in representational memory. *Neuroscience Letters*, 116, 184–189.

Ordy, J. M., Thomas, G. J., Volpe, B. T., Dunlap, W. P., and Colombo, P. M. (1988). An animal model of human–type memory loss based on aging, lesion, forebrain ischemia, and drug studies with the rat. *Neurobiology of Aging*, 9:667–683.

Potter, L. T., Pearce, B. D., and Fisher, A. (1990). Selection of cholinergic agents which may improve memory; In: T. Nagatsu (Ed.), *Basic, clinical and therapeutic aspects of Alzheimer's and Parkinson's diseases*, New York: Plenum Press, 335–340.

Potter, L. T. and Ferrendelli, C. A. (1989). Affinities of different cholinergic agonists for the high and low affinity states of hippocampal M1 muscarine receptors. *Journal of Pharmacology and Experimental Therapeutics*, 248:974–978.

Raffaele, K. C., Berardi, A., Asthana, S., Morris, P., Schapiro, M. B., Haxby, J. V., and Soncrant, T. T. (1991). Performance improvements in patients with dementia of the Alzheimer type following treatment with the muscarinic cholinergic agonist arecoline.*Society for Neuroscience Abstracts*, 274.7.

Sitaram, N. and Weingartner, H. (1978). Human serial learning: enhancement with arecholine and choline and impairment with scopolamine. *Science*, 201:274–276.

Small, G. W. (1992). Tacrine for treating Alzheimer's disease. *Journal of American Medical Association*, 268(18):2564–2565.

Soncrant, T. T., Greig, N. H., Asthana, S., Shetty, H. U., Daly, E., Raffaele, K. C., Berardi, A., and Haxby, J. V. (1992). Optimizing arecoline–induced improvement in Alzheimer's disease by plasma drug monitoring, *Neurobiology of Aging*, 13(suppl 1): s131.

Spencer, D. G., Horvath, E., and Traber, J. (1986). Direct autoradiographic determination of M1 and M2 muscarinic acetylcholine receptor distribution in the rat brain: relation to cholinergic nuclei and projections. *Brain Research*, 380:59–68.

Squire, L. R. (1992). Memory and the hippocampus:a synthesis from findings with rats, monkeys, and humans. *Psychological Review*, 99(2):195–231.

Squire, L. R. and Butters, N. (1992). *Neuropsychology of memory* (2nd ed.), New York: Guilford Press.

Thomas, G. J. and Ordy, J. M. (1992). Memory: a behavioristic and neuroscientific approach. In: L. R. Squire (Ed.), *Neuropsychology of memory* (2nd ed.), New York: Guilford Press, 485–495.

Ordy, Neurobiology of Ageing 9, 667–683 (1988).

Welsh, Arch. Neurol. 48, 278–281 (1991).

Gray, TiPS, Suppl, 85–89 (1989).

Asthana, Soc. for Neurosci 21st Annual Meeting New Orleans, LA Nov. 10–15 1991 Abs #274.7.

Bartus, *Science*, 217, 408 (1982).

Quirion, TiPS, (Suppl) 80–84 (1989).

Mash, Science 228, 1115 (1985).

Pearce, Alzheimers Disease & Related Disorders vol 5, #3, pp. 163–172 (1990).

Washington Post article, Dec. 4, 1991.

Washington Post article, Mar. 19, 1993.

Thompson, New Eng. J. Medicine 323, p. 445.

Kolata, New York Times Article, Jul. 16, 1991.

Nordberg et al. in Alz. Dis & Related Disorders (1989), p. 1169.

Pomara et al, in "Alzheimer's Disease and Related Disorders" (Alan R. Liss, Inc., 1989) pp. 1223–1233.

SPIROFURANE DERIVATIVES

This is a continuation of application Ser. No. 08/304,422 filed on Sep. 12, 1994, abandoned, which, in turn, is a continuation of Ser. No. 08/028,681, filed Mar. 8, 1993, abandoned, which, in turn, is a continuation of application Ser. No. 07/629,797, filed Dec. 19, 1990, abandoned, which, in turn, is a continuation-in-part of International Application No. PCT/US/03351, filed Jun. 20, 1990, which, in turn, is a continuation-in-part of application Ser. No. 07/369,324, filed Jun. 21, 1989, now U.S. Pat. No. 5,075,317.

This invention relates to novel chemical compounds, processes for their preparation, pharmaceutical compositions containing them, and methods of treatment involving their use.

According to the invention there are provided compounds of formula I,

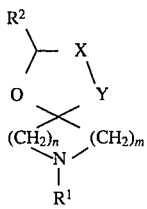

wherein $R^1$ represents hydrogen or alkyl $C_{1-3}$, $R^2$ represents hydrogen or alkyl $C_{1-6}$, alkenyl $C_{3-6}$ or alkynyl $C_{3-6}$, n and m are integers from 1 to 3, provided that n+m=4, and one of X and Y represents $CH_2$ and the other represents $CHR^3$, $C=CHR^4$ or $C=NR^5$, in which $R^3$ represents $NR^6R^7$, $NR^8R^9$, $CO_2R^{10}$, 3-methyl-1,2,4-oxadiazol-5-yl or 3-amino-1,2,4-oxadiazol-5-yl, $R^4$ represents alkanoyl $C_{1-6}$ or $COOR^{11}$, and $R^5$ represents $OR^{12}$, alkanoyloxy $C_{1-6}$, benzoyloxy, $C_{1-6}$ alkanoylamino, $OCONR^{13}R^{14}$, $NHCONR^{15}R^{16}$ or $NHCOOR^{17}$, $R^6$ represents $C^{1-6}$ alkanoyl or $C_{1-6}$ alkoxycarbonyl, $R^7$, $R^8$, $R^9$, $R^{10}$, $R^{11}$, $R^{13}$, $R^{14}$, $R^{15}$, $R^{16}$ and $R^{17}$ represent hydrogen or $C_{1-6}$ alkyl, and $R^{12}$ represents hydrogen, $C_{1-6}$ alkyl, $C_{3-6}$ alkenyl or $C_{3-6}$ alkynyl.

Also included within the scope of the present invention are salts and solvates of the compounds of formula I. It will be appreciated that salts of the compounds for use in medicine will be non-toxic pharmaceutically acceptable salts. Other salts may, however, be useful, in the preparation of the compounds of formula I or their non-toxic pharmaceutically acceptable salts. Acid addition salts, for example, may be formed by mixing a solution of the compound of formula I with a solution of a pharmaceutically acceptable non-toxic acid-such as hydrochloric acid, fumaric acid, maleic acid, succinic acid, carbonic acid or phosphoric acid.

Solvates of the compounds of formula I and their salts include in particular, hydrates of the salts, for example, hemihydrates and monohydrates.

Alkyl groups which $R^2$, $R^7$, $R^8$, $R^9$, $R^{10}$, $R^{11}$, $R^{12}$, $R^{13}$, $R^{14}$, $R^{15}$, $R^{16}$ and $R^{17}$ may represent include methyl, ethyl, n-propyl, iso-propyl, n-butyl, iso-butyl, s-butyl and t-butyl. We prefer compounds, however, in which $R^2$ represents hydrogen or methyl.

Alkenyl groups which represent $R^2$ and $R^{12}$ may represent include 2-propenyl, 2-butenyl and 2-methyl-2-propenyl.

Alkynyl groups which $R^2$ and $R^{12}$ may represent include 2-propynyl and 2-butynyl.

Alkyl groups which $R^1$ may represent include methyl, ethyl, n-propyl and iso-propyl. We particularly prefer compounds in which $R^1$ represents methyl.

We prefer compounds of formula I or a pharmaceutically active salt thereof, in which;

Y represents $CH_2$;

m represents 2;

n represents 2;

$R^1$ represents hydrogen or methyl;

$R^2$ represents hydrogen or methyl;

X represents $C=NR^5$ and $R^5$ represents, $OR^{12}$, alkanoyloxy $C_{1-6}$, $C_{1-6}$ alkanoylamino, $NHCOOR^{17}$ or $OCONR^{13}R^{14}$ in which $R^{13}R^{14}$ and $R^{17}$ are $C_{1-6}$ alkyl.

A more preferred group of compounds are those in which $R^5$ represents $OR^{12}$.

Substituents which are not readily inactivated by hydrolysis in vivo are also preferred.

Many of the compounds of the present invention have at least one asymmetric centre and can therefore exist as enantiomers, and in some cases as diastereomers. Many of the compounds of the present invention contain carbon-carbon and carbon-nitrogen double bonds and can therefore exist as stereoisomers. It is to be understood that the invention covers all such isomers and mixtures thereof.

The compounds of the present invention are useful because they possess pharmacological activity in animals. In particular, the compounds stimulate central muscarinic acetylcholine receptors as can be demonstrated in studies of the affinity constants of the compounds for [$^3$H]-oxotremorine-M binding sites in rat cortical membrane preparations. The compounds may therefore be useful in the treatment of neurological and mental illnesses whose clinical manifestations are due to involvement of specific populations of cholinergic neurones. Such diseases include presenile and senile dementia (also known as Alzheimer's disease and senile dementia of the Alzheimer type respectively), Huntington's chorea, tardive dyskinesia, hyperkinesia, mania and Tourette Syndrome. The compounds are also useful analgesic agents and therefore useful in the treatment of severe painful conditions such as rheumatism, arthritis, and terminal illness.

Thus, according to another aspect of the invention, there is provided a method of treatment of a condition selected from the group consisting of presenile and senile dementia, Huntington's chorea, tardive dyskinesia, hyperkinesia, mania and Tourette Syndrome, which method comprises administering to a patient suffering from that condition a therapeutically effective quantity of one or more compounds of formula I.

Biochemical procedures for measuring affinity and estimating efficacy at brain muscarinic receptors are indicative of the potential utilities for these compounds.

Based largely on the selectivity of the antagonist, pirenzepine, muscarinic receptors have been classified as M1(high affinity for pirenzepine) and M2(low affinity). Brain receptor subtypes appear pharmacologically similar to those in peripheral ganglia(M1) and heart(M2). Receptor subtypes are coupled preferentially to different second messengers and ion channels. Thus in brain as well as other tissues, M1 receptors stimulate phosphatidyl inositol(PI) hydrolysis while M2 receptors inhibit adenylate cyclase. From the results of animal experiments it is suggested that muscarinic agonists having M1 receptor selectivity may be advantageous in improving impaired performance, memory retention and other clinical manifestations of senile dementia.

Two binding assays are used to estimate the affinity and predict the efficacy of test compounds at muscarinic receptors in rat cerebral cortex.

The procedure is described in detail by Freedman, SB, Harley, EA, and Iversen LL, in Br. J. Pharmacol. 93: 437–445 (1988). A rat brain crude membrane preparation is incubated with a radiolabeled antagonist [([$^3$H]N-Methylscopolamine)(NMS)] or agonist [([$^3$H]Oxotremorine-M) (Oxo-M)] and various concentrations of test compound at 30° C. for 40 and 60 minutes, respectively. The membranes are then collected by vacuum filtration on filters and receptor bound radioactivity is determined by liquid scintillation spectroscopy. The affinities (Ki) of the test compound for the agonist high affinity state (radiolabeled agonist) and high and low agonist affinity states together (radiolabeled antagonist) are determined from the competition binding curves using a nonlinear iterative curve fitting computer program. The ratio of measured dissociation constants (the Ki's) are also used as an index of agonist efficacy. Full agonists such as carbachol exhibit an antagonist/agonist ratio of >1800. Partial agonists show a range of ratios extending from 20 to 1500. Antagonists have ratios from 1 to 10.

Compounds of the formula I with a high affinity for the Oxo-M binding site with a Ki of less than 1 μm and preferably less than 0.1 μm and a NMS-Ki/Oxo-M-Ki ratio of greater than 100 are preferred.

In a procedure for measuring agonist efficacy at M1 muscarinic receptors in rat brain hippocampus the muscarinic cholinergic agonist activity of a test compound is measured using an in vitro M1 muscarinic receptor linked enzyme assay which measures the formation of inositol phosphate from phosphatidyl inositol. The assay procedure is described in detail by Fisher SK and Bartus RT, J. Neurochem. 45: 1085–1095(1985). Rat brain hippocampal tissue was cross sliced into 350×350 um segments which were equilibrated for one hour at 37° C. in oxygenated Krebs-Hensleit buffer. Aliquots of slices were then incubated with [$^3$H]myo-inositol, lithium chloride, and various concentrations of test compound for 120 minutes in a 95% $O_2$/5% $CO_2$ atmosphere at 37° C. The reaction is terminated by addition of chloroform/methanol solution (1:2, v/v) and the [$^3$H]inositol phosphates were extracted into the aqueous phase. [$^3$H]Inositol phosphates were purified by ion exchange chromatography using Dowex AG-1×8 anion exchange resin in the formate form. Inositol phosphates were selectively eluted from the resin with a 1M ammonium formate 0.1M formic acid solution. Tritium was determined by liquid scintillation spectroscopy. The magnitude of stimulation of inositol phosphate formation by high concentrations of full agonists such a carbachol was assigned a value of 100%. Partial agonists produced a maximal rate of inositol phosphate formation which varied, according to the compound, from 10 to 80%. Weak partial agonists and antagonists did not stimulate the formation of inositol phosphates.

Compounds of formula I with a maximal rate of inositol phosphate formation of greater than 15% are preferrred.

Partial agonists identified in the above assays may be tested for any selectivity for M1 versus M2 receptors. A measure of M2-receptor mediated inhibition of adenylate cyclase in rat heart membranes can be obtained according to procedures described by Ehlert, F. J. et al[J Pharmacol. Exp. Ther. 228:23–29(1987)].

Some of the compounds may possess muscarinic antagonist properties and thus may be useful as antisecretory agents in the management of peptic ulcers and acute rhinitis, or in the treatment of motion sickness and parkinsonism.

The compounds of the invention may be administered by any convenient route, eg orally, parenterally or rectally. The daily dose required will of course vary with the particular compound used, the particular condition being treated and with the severity of that condition. However, in general a total daily dose of from about 0.1 to 10 mg/kg of body weight, preferably about 0.1 to 1 mg/kg is suitable, administered from 1 to 4 times a day.

For use in the method of treatment of the invention the compound of formula I will generally be administered in the form of a suitable pharmaceutical composition. Thus, according to another aspect of the invention, there is provided a pharmaceutical composition comprising a compound of formula I in admixture with a pharmaceutically acceptable carrier.

The pharmaceutical composition is preferably in unit dose form. Such forms include solid dosage forms, eg tablets, pills, capsules, powders, granules, and suppositories for oral, parenteral or rectal administration, and liquid dosage forms, eg sterile parenteral solutions or suspensions, suitably flavoured syrups, flavoured emulsions with edible oils such as cottonseed oil, sesame oil, coconut oil and peanut oil, and elixirs and similar pharmaceutical vehicles.

Solid compositions may be prepared by mixing the active ingredient with pharmaceutical carriers, eg conventional tabletting ingredients such as corn starch, lactose, sucrose, sorbitol, talc, stearic acid, magnesium stearate, dicalcium phosphate, gums and other diluents, eg water, to form a homogeneous preformulation composition in which the active ingredient is uniformly dispersed so that it may be readily subdivided into equally effective unit dosage forms containing typically from 0.1 to about 500 mg of the active ingredient. The solid dosage forms may be coated or otherwise compounded to prolong the action of the composition.

In order to reduce unwanted peripherally mediated side effects, it may be advantageous to include in the composition a peripherally acting cholinergic antagonist (or anti-muscarinic agent) such as N-methylscopolamine, N-methylatropine, propantheline, methantheline or glycopyrrolate.

According to the invention there is also provided a process for the preparation of compounds of formula I or pharmaceutically acceptable salts or solvates thereof, which comprises a) preparing a compound of formula I in which X or Y represents $CHR^3$ in which $R^3$ is $NR^6R^7$, by reacting a corresponding compound in which $R^3$ is $NHR^7$ with a $C_{1-6}$ alkanoic acid anhydride, $C_{1-6}$ alkanoyl halide or a $C_{1-6}$ haloformate ester, or b) preparing a compound of formula I in which X or Y represents $CHR^3$ in which $R^3$ is $COOR^{10}$, by oxidation of the corresponding compound in which X or Y represents CH—CHO, or c) preparing a compound of formula I in which X or Y represents $CHR^3$ in which $R^3$ is $NRSR^9$, by reacting a corresponding compound in which X or Y represents carbonyl and $R^1$ is a protecting group with a compound of formula $HNR^8R^9$ or $H_2NOH$ in the presence of a reducing agent, or d) preparing a compound of formula I in which X or Y represents $CHR^3$ in which $R^3$ is a 1,2,4-oxadiazol-5-yl group substituted by methyl or amino by reacting a corresponding compound in which $R^3$ is $COOR^{10}$ with an amidine of the formula

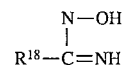

in which $R^{18}$ represents methyl or amino, or e) preparing a compound of formula I in which X or Y represents $C=CHR^4$ by reacting the corresponding compound in which X or Y represents carbonyl with a Wittig reagent of the formula $R^4$—$CH_2P$ in which P represents a suitable phosphonium radical, or f) preparing a compound of formula I in which X or Y represents $C=NR^5$ in which $R^5$ is alkanoyloxy $C_{1-6}$, benzoyloxy or $OCONR^{13}R^{14}$ by reacting the corresponding compound in which $R^5$ is OH with an appropriate acid anhydride, acyl halide or aminocarbonyl halide, or g) preparing a compound of formula I in which X or Y represents $C=NR^5$ in which $R^5$ is $OR^{12}$, $C_{1-6}$ alkanoylamino, $NHCONR^{15}R^{16}$ or $NHCOOR^{17}$ by reacting the corresponding compound in which X or Y represents carbonyl with a nitrogen nucleophile of the formula $H_2N$—$OR^{12}$, H N—$CONHNR^{15}R^{16}$, $H_2N$—$NHCOR^{19}$ in which $R^{19}$ is alkyl $C_{1-5}$ or $H_2NNHCOOR^{17}$, or h) removing a protecting group from a compound of formula I in which one or more of the amino or carboxylic acid groups is protected, or i) preparing a pharmaceutically acceptable salt of a compound of formula I by treating a compound of formula I with an appropriate acid or preparing a free base of a compound of formula I by treating the acid addition salt with a stronger base.

In the reaction of process (a), conventional acylation techniques for amines may be used by reacting with acid halides, acid anhydrides or haloformate esters, for example, acetic anhydride, acetyl chloride, benzoic anhydride or ethyl chloroformate. The reactions may be carried out in the absence of a solvent; however, a suitable inert solvent may be used, for example, toluene, methylene chloride or tetrahydrofuran. The reactions may be carried out at a temperature of, for example from 0°–100° C.

In process (b) oxidation of the aldehyde is carried out with a suitable oxidizing agent, for example, perchloric acid in a protic solvent, for example, methanol. The reaction may be carried out at a temperature of, for example, from 20°–100° C.

The starting material for the oxidation reaction may be prepared from the corresponding compound in which X or Y represents a carbonyl by reaction with an aldehyde synthon, for example, 2-trimethylsilyl-1,3-dithiane, in the presence of a base, for example, butyl lithium in an aprotic solvent, for example hexane or tetrahydrofuran or mixtures thereof and at temperature of, for example, from –20°–30° C. Removal of the masking group to form the corresponding aldehyde is carried out in a suitable solvent, preferably a protic solvent, for example methanol, with a demasking agent, for example, mercuric chloride and at temperatures of, for example, from 0°–100° C.

In process (c), the reaction with the amine is carried out in a protic solvent, for example, methanol or ethanol. The reduction may be carried out with a nucleophilic reducing agent, for example, a complex metal hydride such as sodium (2-methoxyethoxy) aluminum hydride, lithium aluminum hydride, sodium borohydride or sodium cyanoborohydride. The reduction may be carried out in a suitable solvent. Aprotic solvents, for example, tetrahydrofuran are preferred for the aluminum hydrides while protic solvents, for example, methanol or ethanol are preferred for the boron hydrides. The reaction with the nitrogen nucleophile and the reduction reactions may be carried out at a temperature of, for example, from 0°–100° C.

The reaction of process (d) may be carried out in the presence of a base, for example, sodium hydride in an inert solvent, at a temperature of, for example, from 0°100° C. Aprotic solvents are preferred, for example, tetrahydrofuran.

The reaction of process (e) may be carried out in the presence of a base, for example, sodium hydride, in a suitable inert solvent, for example, 1,2-dimethoxyethane and at a temperature of, for example, from 0°–50° C. Reagents which formula $$R^4—CH_2—P$$

may represent include, trimethyl phosphonacetate and triphenyl phosphoranylidene-1-propanone.

In the reaction of process (f), conditions similar to those used in process (a) may be used.

The reaction of process (g) may be carried out with the nitrogen nucleophile in a suitable solvent at a temperature of, for example, from 0°–100° C. Protic solvents are preferred, for example, methanol or ethanol.

In the reaction of process (h), removal of the protecting group depends on the nature of the protecting group and includes acidic or basic cleavage or hydrogenolysis. Suitable amine protecting groups are, for example, ethoxycarbonyl, benzyloxycarbonyl, t-butyloxycarbonyl or $C_{1-3}$ alkanoyl.

In process (i), the salts may be formed by reacting the free base, or a salt or derivative thereof with one or more equivalents of the appropriate acid. The reaction may be carried out in a solvent in which the salt is insoluble or in which the salt is soluble or in mixtures of the solvents.

The starting materials in which X or Y is carbonyl can be prepared by a variety of methods, for example j) oxidation of the corresponding compound in which X or Y represents CHOH.

Conventional oxidation techniques for secondary alcohols may be used in a suitable solvent. A preferred oxidizing agent is that of a mixture of oxalyl chloride and dimethylsulfoxide in a suitable inert solvent, for example, methylene chloride. The reaction may be carried out at a temperature of, for example, from –80°–30° C.

k) reacting the corresponding compound in which $R^1$ is a protecting group and the carbonyl group is protected as a ketal with a reducing agent and subsequent deprotection by hydrolysis of the ketal.

Ketal protection and deprotection of the ketone is effected by conventional methods, for example, with 1,2-dihydroxy ethane in the presence of an acid, for example, p-toluene sulfonic acid to form the ketal and by aqueous acid hydrolysis for removal of the ketal group. Reduction of the nitrogen protecting group, for example, a $C_{1-3}$ alkanoyl or alkoxycarbonyl may be carried out with a hydride reducing agent, for example, diborane or sodium bis (2-methoxyethoxy) aluminum hydride in an aprotic solvent, for example, tetrahydrofuran. The reduction may be carried out at a temperature of, for example, from 0°–100° C.

l) compounds in which $R^2$ represents $C_{3-6}$ alkenyl or $C_{3-6}$ alkynyl and X represents carbonyl may be prepared by reacting the corresponding compound in which $R^2$ represents hydrogen with compounds of the formula $R^{20}$—CH=CH—$CH_2Z$ or $R^{20}$—C≡C—$CH_2Z$ in which $R^{20}$ represents $C_{1-3}$ alkyl and Z represents a halogen;

The reaction may be carried out in the presence of a base, for example, sodium hydride, sodium amide or potassium t-butoxide in a suitable solvent, for example, 1,2-dimethoxyethane, ether, toluene or t-butylalcohol and at a temperature of from –80°–100° C.

m) preparing a compound of the formula I in which X represents C=O, Y represents $CH_2$, $R^2$ represents H or $C_{1-6}$ alkyl, and $R^1$ is a protecting group, by cyclizing a compound of the formula II.

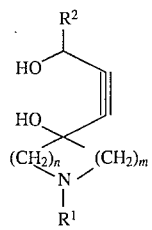

This reaction may be carried out by metal catalyzed cylization according to procedures similar to those described by Saimoto, et al [J. Amer. Chem. Soc. 103, 4975–4977(1981)]. A preferred metal is mercury (II) which may be used in the form of a polymer agent, for example, mercury Nafion-H in aqueous alcoholic solvents, for example, aqueous ethanol, at a temperature of, for example, 0°100° C. Nafion-H is a perfluorinated ion-exchange membrane.

n) preparing a compound of the formula I in which

X represents $CH_2$, Y represents CO, $R^2$ represents H or $C_{1-6}$ alkyl, and $R^1$ is a protecting group, by 1) acetylating a compound of formula II to give a compound of formula III

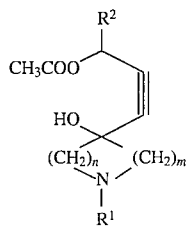

2) cyclizing a compound of the formula III to a compound of formula IV

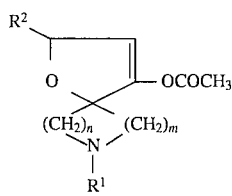

3) selectively hydrolyzing the enol acetate group of the compound of formula IV.

Acetylation of a compound of formula II is effected by conventional methods, for example, with acetic anhydride in pyridine. Cyclization may be carried out by metal catalyzed cyclization according to methods similar to those described by Saimoto, et al. (see infra). A preferred metal is silver (I) which may be used in the form of an inorganic salt, for example, silver perchlorate in an aprotic solvent, for example, toluene at a temperature of, for example, from 20° C.–120° C. Hydrolysis of the enol acetate is effected under mild basic conditions with aqueous alkali, for example, lithium hydroxide in aqueous tetrahydrofuran, at a temperature of, for example, from 0°–50° C.

o) preparing a compound of the formula I in which

X represents CHOH, Y represents $CH_2$, $R^2$ represents H or $C_{1-3}$ alkyl, and $R^1$ represents a protecting group by cyclizing a compound of the formula V.

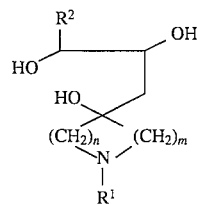

Cyclization may be carried out in the presence of a base in a suitable inert solvent or the base may be used in the absence of a solvent. A suitable base may be an organic amine, for example, pyridine. Cyclization may be facilitated by concomitant derivatization of the alcohol to form a better leaving group, for example, the p-toluene sulfonate ester may be formed by adding p-toluene sulfonyl chloride to the reactants. The reaction may be carried out at a temperature of, for example, 0°–100° C.

The starting materials for the cyclization reactions m, n and o can be prepared by a variety of methods which include, p) preparing a compound of the formula II as defined above by reacting a compound of the formula VI,

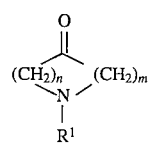

in which $R^1$ is a protecting group with a compound of the formula

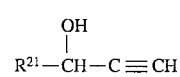

in which $R^{21}$ is H or $C_{1-6}$ alkyl.

The reaction may be carried out in the presence of a base, for example, butyl lithium in an inert aprotic solvent, for example, hexane or tetrahydrofuran or mixtures thereof. The reaction may be carried out at a temperature of for example, from −80° C.–10° C.

q) preparing a compound of the formula V as defined above by 1) reacting a compound of the formula VI with a compound of the formula $R^{22}$—CH=CH—$CH_2$MgZ in which $R^{22}$ represents H or $C_{1-6}$ alkyl and Z represents a halogen, for example, chlorine, bromine or iodine to give a compound of the formula VII,

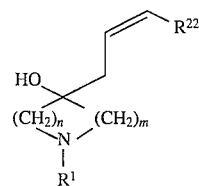

2) epoxidation of the compound of formula VII to the epoxide of formula VIII

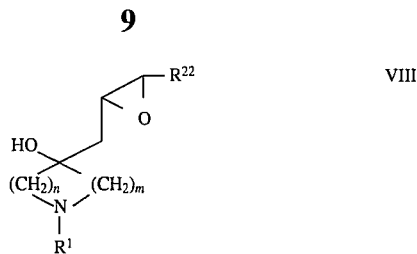

VIII 3) ring-opening of the compound of formula VIII.

The alkylation reaction may be carried out under conventional Grignard reaction conditions, for example, using alkyl magnesium bromide in an inert solvent such as ether or tetrahydrofuran, at a temperature of, for example, from 0°–80° C. The epoxidation reaction may be carried out with an organic per acid or hydrogen peroxide. The organic peracid, for example, m-chloroperbenzoic acid may be used in an inert aprotic solvent, for example, methylene chloride at a temperature of, for example, from 0°–50 ° C. The ring opening of the epoxide may be acid catalyzed, for example, using perchloric acid in a suitable solvent, for example, aqueous tetrahydrofuran, at a temperature of, for example, from 0°–80° C.

The invention will now be illustrated, but in no way limited, by the following Examples in which all temperatures are in degrees Celsius, THF is tetrahydrofuran, DMSO is dimethyl sulphoxide and ether is diethylether. Solvents which are dried before concentration are dried over magnesium sulfate or sodium sulfate. Stereoisomers are designated by the terms Z and E which are synonomous with the terms cis and trans or syn and anti respectively.

EXAMPLE 1

3-Hydroxy-8-methyl-1-oxa-8-azaspiro[4.5]decane hydrochloride a) 1-Ethoxycarbonyl-4-hydroxy-4-(2-propenyl)-piperidine Allyl magnesium bromide was prepared in situ by suspending Mg turnings (21.2 g, 0.87 mol) in dry ether 700 ml) and adding allyl bromide (34.8 g, 0.29 mol) gradually until the reaction initiated and then at sufficient rate to maintain reflux. The reaction was stirred at room temperature for 1.5 hours.

The reaction was cooled to –15° C. with a methanol/ice bath and 1-ethoxycarbonyl-4-piperidinone (25 g, 0.146 mol) was added in ether (700 ml) . The reaction was stirred at room temperature for four hours and then left overnight.

The reaction was cooled with an ice bath while quenching with ammonium chloride (360 ml of a saturated solution diluted to 1440 ml). The reaction was stirred and the phases separated. The aqueous layer was extracted once more with ether and the combined organic layers were washed with brine, dried and stripped. Purification by flash chromatography on silica and elution with CHCl$_3$/NH$_3$, then MeOH/CHCl$_3$/NH$_3$ gave the sub-title compound as a yellow oil (17.2 g).

b) 1-Ethoxycarbonyl-4-hydroxy-4-(2,3-epoxypropyl)-piperidine

The product of step a) (17.2 g, 0.081 mol) was dissolved in dry CH$_2$Cl$_2$ (370 ml) under nitrogen. m-Chloroperbenzoic acid (80%, 35 g, 0.16 mol) was added and the reaction was stirred at room temperature overnight. The white precipitate was removed by suction filtration, and washed with CH$_2$Cl$_2$. The CH$_2$Cl$_2$ was washed with 10% sodium sulphite and this was extracted once with CH$_2$Cl$_2$. The combined organic layers were washed with 10% sodium hydrogen carbonate and this was extracted with CH$_2$Cl$_2$. The combined organic layers were dried over Na$_2$SO$_4$ and stripped. The yellow oil obtained was stored under nitrogen in the freezer. Purification by silica flash chromatography, eluting with MeOH/CHCl$_3$ gave the sub-title compound as a yellow oil (11.1 g).

c ) 1-Ethoxycarbonyl-4-hydroxy-4-(2,3-dihydroxypropyl)-piperidine

The partially purified product of step b) (78.9 g, 0.34 mol) was dissolved in 250 ml of THF and 500 ml of deionized water. Concentrated HClO$_4$ (50 ml) was added and the reaction was stirred overnight. The solution was cooled with an ice bath and neutralized with saturated aqueous NaHCO$_3$. The suspension was then washed with CH$_2$Cl$_2$, and this was back-extracted with H$_2$O.

The aqueous layers were stripped. The resulting residue was digested with four portions of methanol. These were combined, diluted with CHCl$_3$, and dried over Na$_2$SO$_4$. The solvents were stripped and the crude was purified by eluting from silica with an ammoniated methanol/CHCl$_3$ gradient. This gave 37.3 g of brown oil or 13% for the three steps from the ketone.

d) 8-Ethoxycarbonyl-3-hydroxy-1-oxa-8-azaspiro[4.5] decane

The product of step c) (5.2 g, 0.021 mol) was dissolved in dry pyridine (60 ml), placed under nitrogen and cooled with an ice-bath. Tosyl chloride (4.8 g, 0.025 mol) was dissolved in pyridine (30 ml) and added dropwise. The reaction was heated at 110° C. After 5 hours another 2.2 g (0.011 mol) tosyl chloride was added in 20 ml pyridine at room temperature and the heating was continued overnight.

The pyridine was removed as an azeotrope with three portions of toluene and the residue digested seven times with anhydrous ether. The combined organic extracts were filtered and stripped. Purification on silica, flash column using MeOH/CHCl$_3$/NH$_3$ gave the sub-title compound as a colourless oil (1.1 g) . Further ether digestion of the residue, followed by extraction with ether and purification gave a further 1.3 g of product.

e) 3-Hydroxy-8-methyl-1-oxa-8-azaspiro[4.5]decane hydrochloride

The product of step d) (1.3 g, 5.7 mmol) was dissolved in dry THF (60 ml), placed under nitrogen and cooled with an ice bath Vitride (70%, 2.7 ml) in THF (30 ml ) was added dropwise and the reaction stirred at room temperature overnight. Three further portions of Vitride ( 5 ml each) in THF (15 ml each) were added dropwise to the cooled solution and after each portion the solution was stirred for several hours. The reaction was cooled again and treated with 5% NaOH until evolution of hydrogen ceased.

The addition of NaOH was continued at room temperature until a sticky white paste had precipitated. The THF was decanted, suction filtered, and the paste washed once with THF. The solvent was then dried and stripped, and the paste washed once with THF. Purification by silica flash column using MeOH/CHCl$_3$ gave a viscous yellow oil (1.1 g) which partially solidified on standing to white needles. The solid was taken up in isopropyl alcohol and the solution cooled and acidified with HCl/ethanol. This gave a white precipitate which was collected and washed with cold ether to yield the title compound as the hydrochloride salt (0.47 g), mp 228°–229° C.

EXAMPLE 2

8-Methyl-1-oxa-8-azaspiro[4.5]decan-3-one

Oxalyl chloride (1.9 g, 14.3 mmol) was dissolved in dry CH$_2$Cl$_2$ (150 ml) , placed under N$_2$ and cooled to –60 ° C.

with a dry ice/acetone bath. Dry DMSO (2.2 g, 29 mmol) in dry CH$_2$Cl$_2$ (30 ml) was added in slow drops. The reaction was stirred for 10 minutes. The free base of Example 1 (1.5 g, 8.8 mmol) in CH$_2$Cl$_2$ (100 ml) was added in slow drops, the temperature being maintained below −60°. The reaction was stirred for 20 minutes and then was treated dropwise with diisopropylethylamine (9.0 g, 67.5 mmol).

The bath was removed and the reaction allowed to warm somewhat. The solution was treated with distilled water (150 ml) in rapid drops. The layers were separated and the aqueous layer was extracted three times with CH$_2$Cl$_2$. A little saturated Na$_2$CO$_3$ was added and two more CH$_2$Cl$_2$ extractions were done.

The organic layers were dried with Na$_2$SO$_4$ and stripped. Purification by silica flash chromatography, using MeOH/CHCl$_3$/NH$_3$ gave the title product as a yellow oil (1.5 g).

EXAMPLE 2A

8-Methyl-1-oxa-8-azaspiro[4.5]decan-3-one maleate

The yellow oil obtained in Example 2 was taken up in ethyl acetate, the solution cooled in an ice bath and maleic acid/ethyl acetate was added. The title compound was obtained as an off-white powder, mp 127°–128.5°.

|  | C | H | N |
|---|---|---|---|
| Theory: | 54.73 | 6.71 | 4.91 |
| Found: | 54.33 | 6.55 | 4.77 |

NMR (DMSO): δ6.1(2H), 4.0(2H), 3.3(4H,m), 2.8(3H), 2.0(4H,m)
IR (KBr): 2675, 1760, 1580, 1360, 1380, 930 cm$^{-1}$
(M+1)$^+$=170

EXAMPLE 3

8-Methyl-1-oxa-8-azaspiro[4.5]decan-3-one oxime

The compound of Example 2 (0.6 g, 3.5 mmol) was dissolved in methanol (50 ml) and placed under nitrogen. Hydroxylamine hydrochloride was added and the reaction was stirred at room temperature overnight.

The solvent was evaporated, and the residue taken up in CHCl$_3$ and treated with saturated Na$_2$CO$_3$. The layers were separated and the basic layer extracted with three more portions of CHCl$_3$. The combined organic extracts were dried with Na$_2$SO$_4$ and stripped. Purification by silica flash chromatography using MeOH/CHCl$_3$/NH$_3$ gave the title compound as a pale yellow solid.

EXAMPLE 3A

8-Methyl-1-oxa-8-azaspiro[4.5]decan-3 -one oxime maleate

The compound of Example 3 (0.76 g, 4.1 mmol) was dissolved in hot ethyl acetate and mixed with maleic acid (0.48 g, 0.41 mmol) to give the title compound as a white solid, mp 183°–184°.

|  | C | H | N |
|---|---|---|---|
| Theory: | 51.99 | 6.71 | 9.33 |
| Found: | 51.79 | 6.63 | 9.20 |

NMR (DMSO): δ6.1(2H), 4.4(2H), 3.1(4H,m), 2.8(3H), 1.9(4H)
IR (KBr): 3250, 2700, 2450, 1580, 1360, 1380 cm$^{-1}$
(M+1)$^+$=185

EXAMPLE 4

8-Methyl-1-oxa-8-azaspiro[4.5]decan-3-one oxime methyl ether

The ketone of Example 2 (0.5 g, 3 mmol) was dissolved in methanol (30 ml) under a nitrogen atmosphere. Methoxyamine hydrochloride (0.25 g) was added and the solution was stirred at room temperature for 2 hours. Another 0.02 g of reagent was added and stirring was continued for 3 days. The methanol was evaporated and the residue was dissolved in chloroform and washed with saturated aqueous sodium carbonate. The chloroform layer was dried over Na$_2$SO$_4$ and evaporated to give a crude product which was purified by flash chromatography over silica gel and eluted with ammoniated 5% and 10% methanol/chloroform. Concentration of the solvent afforded a residue which was dissolved in ether and treated with fumaric acid dissolved in ether while warming on a steam bath. The precipitated solid was kept at room temperature overnight then it was collected by filtration and washed with ether to give 0.35 g of the fumarate salt, mp 149°–152° C.

|  | C | H | N |
|---|---|---|---|
| Theory: | 53.49 | 7.05 | 8.91 |
| Found: | 53.22 | 7.00 | 8.77 |

EXAMPLE 5

3-Hydroxy-2.8-dimethyl-1-oxa-8-azaspiro[4.5]decane a) 4-(3-Hydroxy-1-butynyl)-1-ethoxycarbonyl-4-piperidinol A solution of 3-butyn-2-ol (42 g, 0.6 mol) in dry THF (800 ml) under nitrogen was cooled with a dry-ice/acetone bath. n-Butyl lithium (390 ml of 2.5M and 230 ml of 1.5M) in hexane was added rapidly, dropwise. The suspension became gelatinous and another 800 mls of dry THF was added. The reaction was stirred at approximately −78° C. for 1 hour and then at 0° C. for 20 minutes. The reaction was cooled to −78° C. and 1-ethoxycarbonyl-4-piperidinone (104 g, 0.607 mol) in 300 ml of dry THF was added rapidly dropwise. The reaction mixture was allowed to warm to room temperature and then stirred overnight. The reaction mixture was cooled in an ice-bath, diluted with THF (1.5l), decomposed with saturated NH$_4$Cl, and the THF layer was washed three times with 200 ml of saturated ammonium chloride. The aqueous layers were back-washed with THF (200 ml×3). The organic layers were combined and dried over MgSO$_4$ and evaporated to give an oil. A one-fifth portion of the oil was purified by flash chromatography on silica gel and elution with 30% ethyl acetate/ether afforded the desired product diol (19.7 g).

b) 8-Ethoxycarbonyl-2-methyl-1-oxa-8-azaspirodecan-3-one

The diol of step a) (19.7 g, 0.082 mol) was dissolved in ethanol (82 ml) and water (7.4 g, 0.41 mol). Mercury/Nafion NR50 (41 g) prepared according to Y Saimoto et al (Bull Chem Soc Japan, 56, 3078 (1983)) was added and the slurry was stirred in a closed flask for three days. The resin was filtered off and washed with methylene chloride. The combined filtrates were evaporated. The residue was dissolved as far as possible in ether and filtered through a bed of silica gel to clarify the solution. The filtrate was evaporated to give the ketone as a yellow oil (13.3 g).

c) 3-Hydroxy-2,8-dimethyl-1-oxa-8-azaspiro[4.5]decane

The ketone from step b) (10.2 g, 0.042 mol) was dissolved in dry THF (375 ml) under nitrogen and cooled in an ice-bath. Vitride (57 ml, 0.021 mol), diluted with THF (450 ml) was added dropwise and the reaction was stirred at room temperature overnight. The reaction was decomposed with water according to the method of example 2(e) and the desired title compound was isolated as an oil.

EXAMPLE 6

2,8-Dimethyl-1-oxa-8-azaspiro[4.5]decan-3-one

The alcohol from Example 5 is oxidized according to the procedure described in Example 2 above to give the title amine.

EXAMPLE 6A 2,8-Dimethyl-1-oxa-8-azaspiro[4.5]decan-3-one fumarate

The amine (2 g) from Example 6 was dissolved in ether and treated with an equivalent amount of fumaric acid dissolved in ether. The precipitated salt was filtered and dried to give the title compound (1.15 g), mp 139°–141° C.

|  | C | H | N |
|---|---|---|---|
| Theory: | 56.18 | 7.07 | 4.68 |
| Found: | 55.95 | 7.06 | 4.68 |

EXAMPLE 6B

Alternative Preparation of 2,8-Dimethyl-1-oxa-8-azaspiro[4.5]decan-3-one a) 8-Ethoxycarbonyl-2-methyl-1-oxa-8-azaspiro[4.5]decan-3-one ethylene ketal 8-Ethoxycarbonyl-2-methyl-1-oxa-8-azaspiro [4.5]decan-3-one (23 g, 0.0963 mol),ethylene ketal (50 ml) and p-toluenesulfonic acid (1 g) were suspended in toluene (500 ml) and refluxed for 3 hours while water and ethylene glycol were collected in a Dean and Stark trap. The solution was cooled, washed with water and the aqueous layer was backwashed with chloroform. The combined solvent layers were dried and concentrated to give the title ketal as a thick oil (25.8 g).

b) 2,8-Dimethyl-1-oxa-8-azaspiro [4.5]decan-3-one ethylene ketal.

The carbamate-ketal from step (a) (10 g, 0.035 mol) in THF (50 ml) was added at room temperature during 30 mins. to a solution of Vitride (0.105 mol) in THF (150 ml). The reaction was stirred for 1 hour then decomposed by the addition of 20 ml of 20% aqueous THF then additional water until a clear supernatant layer formed. The solvent layer was separated and evaporated in vacuo. The residue was chromatographed on silica gel and eluted with 20% MeOH/ $CH_2CL_2$ to give the dimethyl-ethylene ketal as a thick oil (1414 g). A sample of the oil (0.5 g) was converted to the maleate salt in ether and crystallized from methylene chloride/ether to give the salt (0.24 g), mp 105°–108° C.

|  | C | H | N |
|---|---|---|---|
| Theory: | 55.96 | 7.34 | 4.08 |
| Found: | 56.10 | 7.48 | 4.10 | c) 2,8-Dimethyl-1-oxa-8-azaspiro[4.5]decan-3-one maleate

The ketal base from step (c) (14.4 g, 0.0634 mol) dissolved in 1.25N.HCL (100 ml) was heated at 50° C. for 4 hours. The reaction was cooled, basified with saturated aqueous $Na_2CO_3$ solution and the precipitated base was extracted into chloroform. The chloroform solution was dried and the solvent evaporated in vacuo to give the ketone as an oil (13.35 g).

A sample of the oil (4.46 g) was converted to the maleate salt in ether. The precipitated salt was recrystallized twice from ethyl acetate to give the title product (3.11 g), mp 137.5°–139° C.

|  | C | H | N |
|---|---|---|---|
| Theory: | 56.18 | 7.07 | 4.68 |
| Found: | 56.23 | 7.14 | 4.70 |

EXAMPLE 7

1-Oxa-8-azaspiro[4.5]decan-3-one hydrochloride

8-Ethoxycarbonyl-8-azaspiro[4.5]decan-3-one (3.1 g, 0.0136 mol) was dissolved in conc.HCL (25 ml) and heated at reflux for 4 hrs. Toluene was added and the water was removed by azeotroping. The toluene was evaporated in vacuo and the residue was triturated with ether and the ether decanted. The residue was taken up in glacial acetic acid and ether added to precipitate an oil. The supernatatant solvents were decanted. This procedure was repeated four times and a solid precipitate formed. The solid was washed with ether and dried in vacuo to give the title product as the hydrochloride (0.95 g).

|  | C | H | N | Cl |
|---|---|---|---|---|
| Theory: | 49.09 | 7.42 | 7.09 | 17.94 |
| Found: | 49.43 | 7.34 | 6.91 | 17.86 |

EXAMPLE 8

2-Ethyl-8-methyl-1-oxa-8-azaspiro[4.5]decan-3-one maleate a) 8-Ethoxycarbonyl-2-ethyl-1-oxa-8-azaspiro[4.5]decan-3-one Following essentially the same procedure as described in Example 5, steps a and b, and substituting 3-pentyn-2-ol (18.9 g, 19.7 mol) for 3-butyn-2-ol the intermediate 2-ethyl ketone was prepared as an oil (18.7 g).

b) 2-Ethyl-8-methyl-1-oxa-8-azaspiro[4.5]decan-3-one

The crude 2-ethyl ketone (18.7 g) from step (a) was dissolved in 350 ml of toluene under a nitrogen atmosphere. Ethylene glycol (35 ml) and p-toluenesulfonic acid (0.75 g) were added and the reaction was heated at reflux. A Dean & Stark apparatus was used to remove the water. After 3 hrs.

the reaction was cooled with an ice-bath and the toluene layer was washed with cold water. The aqueous layer was back extracted with chloroform and the combined organic layers were dried and evaporated to give the crude ketal as an oil (21.5 g). The ketal (21.5 g, 0.072 mol) was dissolved in THF (220 ml) and added dropwise to Vitride (0.216 mol) in THF (284 ml). The reaction was stirred overnight, cooled and then water was added to decompose the complex and excess Vitride. The THF layer was separated, dried and concentrated to give the crude 8-methyl-ketal (20.8 g). A portion of the ketal (18.8 g, 0.078 mol) was heated with 125 ml of 1.25N.HCL at 50° C. for 3 hrs. The cooled solution was neutralized with saturated $Na_2CO_3$ solution. The aqueous mixture was extracted twice with chloroform, the chloroform layer was dried and concentrated to give the title ketone as an oil (11.6 g).

c) 2-Ethyl-8-methyl-1-oxa-8-azaspiro[4.5]decan-3-one maleate

The crude ketone base (11.6 g) was dissolved in ethyl acetate and a saturated solution of maleic acid (6.8 g) in ethyl acetate was added. The precipitated salt was recrystallized from ethyl acetate to give the maleate salt (8.3 g) m.p. 131°–132.5° C.

|  | C | H | N |
|---|---|---|---|
| Theory: | 57.50 | 7.40 | 4.47 |
| Found: | 57.49 | 7.63 | 4.49 |

EXAMPLE 9

2-Methyl-1-oxa-8-azaspiro[4.5]decan-4-one hydrochloride a) 4-Acetoxy-8-ethoxycarbonyl-2-methyl-1-oxa-8-azaspiro[4.5]-3-decene 1-Ethoxycarbonyl-4-hydroxy-4-(3-acetoxy-1-butynyl) piperidine (14.5 g, 0.051 mol), prepared from the product of Example 8a by acetylation with acetic anhydride/pyridine, was combined with dry toluene (150 ml) and silver perchlorate (0.6 g). The reaction vessel was wrapped in foil and the reaction mixture was heated under nitrogen at 80° C. for 19 hours. A further 0.2 g of silver perchlorate were added and heating was continued for another 5 hours. The cooled solution was diluted with methylene chloride (150 ml) and washed with 450 ml of 10% aqueous ammonium hydroxide. The organic layer was dried and concentrated. The residue was purified by flash chromatography in ammoniated silica gel and eluted with 4% hexane/ether. The enol acetate was isolated, 12.8 g.

b) 2-Methyl-1-oxa-8-azaspiro[4.5]decan-4-one hydrochloride

The enol acetate (3.4 g, 0.012 mol) from step (a) was heated with 15 ml of conc.HCL in 40 ml of toluene at reflux under Dean and Stark conditions. After 3 hours an additional 10 ml of conc.HCL were added and heating was continued for 2 hours. The toluene was evaporated and the residue was heated at reflux with conc.HCL (15 ml) for a further 3 hours and toluene was added to remove the water. Evaporation of the toluene afforded a solid which was triturated with ether to remove impurities. The insolubles were dissolved in isopropanol, treated with charcoal, filtered and the filtrate was concentrated to dryness. The solid residue was stirred in ether and the ether was decanted to leave the title ketone hydrochloride as a solid.

|  | C | H | N | Cl |
|---|---|---|---|---|
| Theory: | 51.83 | 7.89 | 6.72 | 17.00 |
| Found: | 51.34 | 7.74 | 6.64 | 16.72 |

EXAMPLE 10

4-Hydroxy-2,8-dimethyl-1-oxa-8-azaspiro[4.5]decane fumarate a) 4-Ethoxycarbonyl-2-methyl-1-oxa-8-azaspiro[4.5]decan-4-one The enol acetate (12.6 g, 0.044 mol) from Example 9, step (a) was dissolved in THF, under nitrogen and cooled with an ice bath. A solution of lithium hydroxide (1.0 g) in water was added. Water was added until solution was obtained. After 3 hours at 0° C., the reaction was warmed to room temperature and another 2 g of lithium hydroxide were added. The THF phase was separated and the aqueous phase was extracted fruther with THF. The combined extracts were dried and concentrated and the residue was purified by chromatography on silica gel and elution with ammoniated hexane/ethanol(3:7). Evaporation of the solvents afforded the title ketone (8.2 g) which was used directly in the next step.

b) 4-Hydroxy-2,8-dimethyl-1-oxa-8-azaspiro[4.5]decane fumarate

Following essentially the same procedure as in Example 5, step (c), and substituting 8-ethoxycarbonyl-2-methyl-1-oxa-8-azaspiro[4.5]decan-4-one (8.2 g, 0.034 mol) for 8-ethoxycarbonyl-2-methyl-1-oxa-8-azaspiro[4.5]decan-3-one afforded the corresponding 4-hydroxy-2,8-dimethyl-1-oxa-8-azaspiro [4.5 ]decane as an oil (3.4 g). A sample of the oil (1 g) was converted to the fumarate salt by treatment with fumaric acid in ether (124 ml). The precipitated solid was purified by trituration with ethyl acetate mp 161°–168° C.

EXAMPLE 11

2,8-Dimethyl-1-oxa-8-azaspiro[4.5]decane-4-one

Following essentially the same procedure as described in Examples 2 and 2A, and substituting 4-hydroxy-2,8-dimethyl-1-oxa-8-azaspiro[4.5]decane (2.4 g, 0.013 mol) for 3-hydroxy-2,8-dimethyl-1-oxa-8-azaspiro[4.5]decane afforded the corresponding 2,8-dimethyl-1-oxa-8-azaspiro [4.5]decane-4-one maleate (0.9 g), mp 128°–130° C.

|  | C | H | N |
|---|---|---|---|
| Theory: | 56.18 | 7.07 | 4.68 |
| Found: | 56.17 | 7.11 | 4.65 |

EXAMPLE 12

8-Methyl-1-oxa-8-azaspiro[4.5]decan-3-one O-acetyloxime maleate

8-Methyl-1-oxa-8-azaspiro[4.5]decan-3-one oxime (1.6 g 8.7 mmol) and acetic anhydride (50 ml) were heated at reflux under nitrogen for 2½ hours. Excess acetic anhydride was evaporated in vacuo and chased with heptane. The residual syrup was dissolved in chloroform and washed with aqueous sodium carbonate solution. The chloroform layer was dried and evaporated to give a residue which was dissolved in ethylacetate and maleic acid (0.76 g) was added. The precipitated solid was filtered and purified by digestion with hot ethyl acetate to give the title product, mp 154°–158° C. (decomp).

|  | C | H | N |
|---|---|---|---|
| Theory: | 52.00 | 6.54 | 8.06 |
| Found: | 52.29 | 6.32 | 6.92 |

EXAMPLE 13

8-methyl-1-oxa-8-azaspiro [4.5]decan-3-one O-propionyloxime maleate

Following essentially the same procedure as described in Example 12 and substituting propionic anhydride for acetic anhydride and heating at only 50° C. for about 6 hours afforded the title product, mp. 132°–137° C. (decomp.).

|  | C | H | N |
|---|---|---|---|
| Theory: | 53.36 | 6.83 | 7.78 |
| Found: | 53.33 | 6.83 | 7.66 |

EXAMPLE 14

8-Methyl-1-oxa-8-azaspiro[4.5]decan-3-one-O-benzoyloxime maleate

Following essentially the same procedure as described in Example 12 and substituting benzoic anhydride for acetic anhydride, and heating at only 50° C. for 6 hours afforded the title product, mp 147°–150° C.

|  | C | H | N |
|---|---|---|---|
| Theory: | 59.25 | 6.22 | 6.91 |
| Found: | 58.72 | 5.90 | 6.71 |

EXAMPLE 15

2,8-Dimethyl-1-oxa-8-azaspiro[4.5]decan-3-one O-propionyloxime maleate 2,8-Dimethyl-1-oxa-8-azaspiro[4.5]decan-3-one oxime (3 g, 0.015 mol) was heated at 50° C. with propionic anhydride (60 ml) for 3 hours. The excess anhydride was evaporated in vacuo. The residue was dissolved in chloroform and washed with saturated aqueous sodium carbonate. The chloroform layer was dried and evaporated to give an oil which was purified by chromatography on $SiO_2$ and elution with ammoniated 2–10% $MeOH/CHCl_3$. The isolated product was treated with maleic acid in hot ethyl acetate and the salt of the title compound was collected and washed with ether. mp 119°–120° C.

EXAMPLE 16

2,8-Dimethyl-1-oxa-8-azaspiro[4.5]decan-3-one oxime fumarate

Following essentially the same procedure as described for Example 3 and substituting 2,8-dimethyl-1-oxa-8-azaspiro [4.5[decan-3-one (1.4 g, 7.7 mmol) for 8-methyl-1-oxa-8-azaspiro[4.5]decan-3-one afforded the free base as an oil (2.1 g). The oil was dissolved in ethyl acetate and diluted with a saturated solution of fumaric acid in ether. The precipitated solid was filtered and dried to give the title product (1.5 g).

|  | C | H | N |
|---|---|---|---|
| Theory: | 53.49 | 7.05 | 8.91 |
| Found: | 53.48 | 7.24 | 9.55 |

EXAMPLE 17

3-Amino-8-methyl-1-oxa-8-azaspiro[4.5]decane maleate

8-Ethoxycarbonyl-1-oxa-8-azaspiro[4.5]decan-3-one oxime (15.2 g, 0.063 mol) was dissolved in dry THF (400 ml) and added dropwise to a stirred solution of Vitride (71 ml, 0.25 mol) in THF (400 ml) cooled with an ice bath. After stirring the reaction overnight at room temperature additonal Vitride (35 ml) in THF (200 ml) was added and stirring was continued for 24 hours. Decomposition of the complex and excess Vitride with successive addition of water, 15% NaO-Haq and water was carried out. The THF was filtered and evaporated to give the crude amine which was purified by chromatography on silica gel and elution with ammoniated 2–20% $MeOH/CHCl_3$. The crude amine was dissolved in ethyl acetate and maleic acid was added. The precipitated salt was recrystallized from isopropanol/ethyl acetate to give the title product.

|  | C | H | N |
|---|---|---|---|
| Theory: | 50.87 | 6.28 | 6.98 |
| Found: | 50.53 | 6.30 | 6.62 |

EXAMPLE 18

3-Amino-2,8-dimethyl-1-oxa-8-azaspiro[4.5]decane a) 8-Ethoxycarbonyl-2-methyl-1-oxa-8-azaspiro[4.5]decan-3-one oxime 8-Ethoxycarbonyl-2-methyl-1-oxa-8-azaspiro [4.5 ]decan-3-one (20 g, 0.083 mol) was dissolved in absolute ethanol (1 L) and combined with triethylamine (11.5 ml) and hydroxylamine hydrochloride (5.7 g). The mixture was stirred at room temperature overnight. The ethanol was evaporated in vacuo and the residue was stirred with ether. The insoluble solids were filtered and the ether filtrate was evaporated. The residual oxime was purified by chomatography on silica gel and elution with ammoniated 2–10% $MeOH/CHCl_3$. Evaporation of the solvents afforded the oxime, 11.5 g.

b) 3-Amino-2,8-dimethyl-1-oxa-8-azaspiro[4.5]decane maleate

A solution of 8-ethoxycarbonyl-2-methyl-1-oxa-8-azaspiro[4.5]decan-3-one oxime (9.2 g, 0.036 mol) from step (a) in dry THF (180 ml) was added dropwise to a suspension of lithium aluminum hydride (5.5 g, 0.098 mol) and aluminum chloride (0.55 g, 4 mmol) in dry THF (360 ml). The reaction was stirred overnight at room temperature. The reaction was cooled and decomposed by successive addition of water (5.5 ml), 15% ag.NaOH (5.5 ml) and water (16.5 ml). The solids were filtered off and the THF filtrate was concentrated in vacuo. The residual oil was dissolved in chloroform, dried and evaporated. The crude amine was purified by chomatography in silica gel and elution with ammoniated 10–40% MeOH/CHCl$_3$. A 1g sample of the amine was dissolved in hot ethyl acetate and treated wtih maleic acid (1.3 g). The gummy precipitate was dissolved in hot isopropanol and ethyl acetate was added until precipitation began. After 16 hours, the precipitated solid was isolated by filtration and dried to give the title product (1.15 g), mp 115°–120° C. (decomp.).

|  | C | H | N |
|---|---|---|---|
| Theory: | 51.12 | 6.84 | 6.62 |
| Found: | 51.26 | 6.61 | 6.52 |

EXAMPLE 19

(E)- and (Z)-Methyl

2-[2,8-dimethyl-1-oxa-8-azaspiro[4.5] decan-3-ylidine]-acetate maleate

A solution of trimethyl phosphonoacetate (7.4 g, 0.041 mol) in 1,2-dimethoxyethane (30 ml) was added dropwise to a suspension of sodium hydride (2 g, 0.049 mol) in DME (60 ml). After 1 hour, the 2,8-dimethyl-1-oxa-8-azaspiro[4.5] decan-3-one (6 g, 0.0327 mol) in DME (30 ml) was added dropwise at room temperature and the reaction was stirred for 3 hours. The reaction mixture was poured into saturated aqueous Na$_2$CO$_3$ and extracted with chloroform (3 x). The combined extracts were dried and the solvent evaporated to give an oil which was chromatographed in silica gel and eluted with ammoniated CHCl$_3$/EtOAc/MeOH (2/2/1). The major fraction (1.89 g) was converted to the maleate salt in ether and the precipitated solid was recrystallized from ethyl acetate to give 1.59 g of a single (E)-isomer, mp. 134°–135.5° C.

|  | C | H | N |
|---|---|---|---|
| Theory: | 57.45 | 7.09 | 3.97 |
| Found: | 57.26 | 7.09 | 3.90 |

A minor fraction of 1.05 g was converted to the maleate in ether and recrystallized from ethyl acetate to give the (Z)-isomer (0.46 g) mp. 142°–145 ° C.

|  | C | H | N |
|---|---|---|---|
| Found: | 57.05 | 7.36 | 3.84 |

EXAMPLE 20

Methyl

2-[8-methyl-1-oxa-8-azaspiro [4.5 ]decan-3-ylidine]-acetate maleate

Following essentially the same procedure as described in Example 19 and substituting 8-methyl-1-oxa-8-azaspiro [4.5]decan-3-one (0.43 g, 2.5 mmol ) for 2,8-dimethyl-1-oxa-8-azaspiro[4.5 ]decan-3-one afforded the title product (0.2 g), mp. 158–159.5.

|  | C | H | N |
|---|---|---|---|
| Theory: | 56.30 | 6.79 | 4.10 |
| Found: | 55.97 | 6.73 | 4.03 |

EXAMPLE 21

Methyl 2,8-dimethyl 1-oxa-8-azaspiro[4.5]decane-3-carboxylate maleate a) 2,8-Dimethyl-3-(1,3-dithian-2-ylidene)-1-oxa-8-azaspiro[4.5]decane To a solution of 2-(trimethylsilyl)-1,3-dithiane (8.4 g, 0.0436 mol) in THF (70 ml) cooled to 0° C. were added 17.4 ml of a 2.5M solution of n-butyl lithium in hexane dropwise and the solution was stirred for 30 minutes. A solution of 2,8-dimethyl-1-oxa-8-azaspiro[4.5]decan-3-one (4 g, 0.0218 mol) in THF (20 ml) was added dropwise and the reaction was stirred for 2.5 hours to room temperature. Water was added and then the clear supernatant liquid was decanted. Evaporation of the solvent layer afforded an oil which was chromatographed on silica gel and eluted with 5–10% MeOH/CHCl$_3$. Evaporation of the solvents afforded the dithiane product (3.79 g). A portion of the product 10.3 g) was converted to the maleate salt in ether and recrystallized from ethyl acetate, mp. 128.5°–129.5° C.

|  | C | H | N | S |
|---|---|---|---|---|
| Theory: | 53.84 | 6.78 | 3.49 | 15.97 |
| Found: | 53.86 | 6.71 | 3.48 | 16.19 | b) Methyl 2,8-dimethyl-1-oxa-8-azaspiro[4.5]decane-3-carboxylate

A suspension of 2,8-dimethyl-3-(1,3-dithian-2-ylidene)-1-oxa-8-azaspiro[4.5]decane (2.84 g, 9.95 mmol), HgCl$_2$(10.8 g, 0.04 mol) and perchloric acid (60%, 5.2 ml) in MeOH/85 ml) was heated at reflux for 2 hours, cooled and decomposed with saturated aqueous sodium bicarbonate solution. The solids were filtered and the filtrate was extracted with methylene chloride. The organic extracts were dried and evaporated. The residue obtained was chromatographed on silica gel and eluted with ammoniated 10–25% MeOH/CH$_2$Cl$_2$ to give the title ester as an oil (1.39 g). A 1 g sample of the oil was converted to the maleate salt in ether. The crude salt was crystallized from methylene chloride/ether to give the maleate salt of the title product (0.48 g), mp 105°–107° C.

|  | C | H | N |
|---|---|---|---|
| Theory: | 55.97 | 7.34 | 4.08 |
| Found: | 55.86 | 7.23 | 4.04 |

EXAMPLE 22

2,8-Dimethyl-3-(3-methyl-1,2,4-oxadiazol, 5-yl)-1-oxa-8-azaspiro[4.5]decane maleate A mixture of sodium hydride (0.176 g, 0.0044 mol) and N-hydroxy acetamidine (0.36 g, 0.0048 mol) in THF (100 ml) was refluxed for 1 hour. The reaction was cooled, 2 g of molecular sieves (Type 3A) were added followed by methyl 2,8-dimethyl 1-oxa-8-azaspiro[4.5]decane-3-carboxylate (0.5 g, 0.0022 mol) in THF (10 ml). The reaction was heated at reflux for 3 hours and kept at room temperature overnight. Water was added followed by saturated aqueous $Na_2CO_3$ and the mixture was extracted with chloroform. The solvent was dried and evaporated to give an oil which was chromatographed on silica gel and eluted with ammoniated 10% MeOH/$CHCl_3$ to give an oil (0.4 g). The oil was treated with maleic acid in ether and the precipitated solid was recrystallized form ethyl acetate/ether to give the title product (0.3 g), mp 106°–108 ° C.

|  | C | H | N |
|---|---|---|---|
| Theory: | 55.58 | 6.86 | 11.44 |
| Found: | 55.65 | 7.13 | 11.35 |

EXAMPLE 23

3-Acetamido-2,8-dimethyl-1-oxa-8-azaspiro[14.5]decane fumarate

3-Amino-2,8-dimethyl-1-oxa-8-azaspiro [4.5]decane (1 g, 5.4 mmol) was heated with acetic anhydride (5 ml) under $N_2$ at 50 ° C. for 3 hours. The excess acetic anhydride was distilled in vacuo and the residue was dissolved in $CHCl_3$. The chloroform layer was washed with aq.$Na_2CO_3$, dried and evaporated. The crude product was purified by chromatography on silica gel and eluted with ammoniated 2–20%. MeOH/$CHCl_3$ to give an oil (0.75 g). The oil was treated with fumaric acid in ether to give the title product mp 143°–147° C.

|  | C | H | N |
|---|---|---|---|
| Theory: | 56.07 | 8.38 | 9.03 |
| Found: | 55.53 | 8.06 | 8.39 |

EXAMPLE 24

2,8-Dimethyl-3-(dimethylamino)-1-oxa-8-azaspiro[4.5] decane maleate a) 8-(Ethoxycarbonyl)-2-methyl-3-(dimethylamino)-1-oxa-8-azaspiro[4.5]decane 8-(Ethoxycarbonyl)-2-methyl-1-oxa-8-azaspiro [4.5]decan-3-one (12 g, 0.05 mol) was combined with sodium cyanoborohydride (3 g, 0.05 mol) in absolute ethanol (150 ml) in a steel bomb. Dimethylamine (32 ml, 0.45 mol) was added, then a saturated HCl/EtOH solution was added until pH7 was reached. The bomb was sealed and heated at 60° C. overnight. An additional 20 ml of dimethylamine were added and the reaction was heated at 60° C. for 8 hours. After cooling to room temperature and standing overnight the solution was acidified to pH2 with conc.HCl. The solution was concentrated in vacuo and the residue was dissolved in water. The solution was basified to pH10 with KOH pellets then the precipitated base was extracted into chloroform. The chloroform solution was dried and concentrated. The residue was purified by chromatography in silica gel and eluted with ammoniated 2–5% McOH/$CHCl_3$ to give the title amine-carbamate.

b) 2,8-Dimethyl-3-(dimethylamino)-1-oxa-8-azaspiro [4.5]decane maleate

8-Ethoxycarbonyl-2-methyl-3-(dimethylamino)-1-oxa-8-azaspiro[4.5]decane (11.9 g, 0.044 mol) dissolved in THF (135 ml) was added dropwise to a solution of Vitride (172 ml, 0.126 mol). The reaction was stirred for 4 hours at room temperature then at reflux for 30 minutes. After cooling with an ice-bath, the reaction was quenched by the addition of water. The supernatatant THF solution was decanted, dried and concentrated. The residue of crude product was purified by filtration through a bed of silica gel and elution with ammoniated MeOH/$CHCl_3$. The filtrate was evaporated to give the title amine as a yellow oil (5.7 g). The oil was converted to the maleate salt by treatment with maleic acid in ethyl acetate. The oily salt obtained was crystallized from isopropanol/ethylacetate to give the maleate salt (5.7 g), mp 127°–130° C.

|  | C | H | N |
|---|---|---|---|
| Theory: | 54.05 | 7.26 | 6.30 |
| Found: | 53.92 | 7.47 | 6.28 |

EXAMPLE 25

(2,8-Dimethyl-1-oxa-8-azaspiro[4.5]decan-3-yl) carbamic acid ethyl ester

Ethyl chloroformate was added to 3-Amino-2,8-dimethyl-1-oxa-8-azaspiro[4.5]decane (1 g 5.4 mmol) in THF (20 ml). An additional 20 ml of THF were added and the reaction was stirred for 2 hours at room temperature. The THF solution was mixed with saturated sodium carbonate solution and the THF layer was separated, dried and evaporated to give a product which was purified by chromatography on silica gel and eluting with 5–10% ammoniated MeOH/$CHCl_3$. The major fraction was converted to the fumaric acid salt in ether but a solid could not be obtained. The salt was neutralized with aqueous alkali and the base was extracted into methylene chloride. Concentration of the methylene chloride afforded the title carbamate compound as an oil.

EXAMPLE 26

N-Acetyl-2,8-dimethyl-1-oxa-8-azaspiro[4.5]decan-3-one hydrazone 2,8-Dimethyl-1-oxa-8-azaspiro[4.5]decan-3-one (1.0 g, 5.5 mmol) was combined with acetic hydrazide (0.5 g, 6.7 mmol) and absolute ethanol (50 ml). Ethanolic HCL was added to pH5 and then the reaction was stirred at room temperature overnight. The ethanol was evaporated in vacuo and the residue was dissolved in $CHCl_3$. The chloroform solution was washed with saturated $Na_2CO_3$. The $CHCl_3$ layer was evaporated to dryness. The crude product was purified by chromatography on silica gel and elution with ammoniated 2–20% MeOH/$CHCl_3$ to give 0.86 g of a yellow solid. The solid was dissolved in hot ethyl acetate and maleic acid (0.42 g) was added. The precipitated solid was filtered to give the title compound (0.98 g), mp 164°–167° C.

|  | C | H | N |
|---|---|---|---|
| Theory: | 54.08 | 7.04 | 11.64 |
| Found: | 53.86 | 7.03 | 11.60 |

EXAMPLE 27

2,8-Dimethyl-1-oxa-8-azaspiro[4.5]decan-3-one semicarbazone maleate 2,8-Dimethyl-1-oxa-8-azaspiro[4.5]decan-3-one (1.0 g, 5.5 mmol) and semicarbazide hydrochloride (1 g) were dissolved in abs. EtOH (50 ml). The reaction was stirred at room temperature overnight. The reaction was concentrated in vacuo and the residue was dissolved in chloroform and washed with saturated $Na_2CO_3$. The chloroform layer was dried and concentrated to give the crude product which was purified by chromatography on silica gel and elution with ammoniated 2–10% $MeOH/CHC_3$. The solid obtained (1.4 g) was converted to the maleate salt in hot ethyl acetate. The resulting solid was digested with hot ethyl acetate and dried to give the title product, mp 204°–206° C.

|  | C | H | N |
|---|---|---|---|
| Theory: | 50.56 | 6.79 | 15.72 |
| Found: | 50.62 | 6.73 | 15.41 |

EXAMPLE 28

Preparation of (E)-and(Z)-2,8-Dimethyl-1-oxa-8-azaspiro [4.5]decan-3-one oxime methyl ether maleates.

2,8-Dimethyl-1-oxa-8-azaspiro[4.5]decan-3-one (5 g, 0.027 mol) was dissolved in absolute ethanol (200 mL) and pyridine (0.44 mL) was added. Methoxyamine hydrochloride (2.5 g, 0.03 mol) was added and the reaction mixture was stirred overnight. The ethanol was evaporated and the residue was dissolved in $CHCl_3$ and partitioned with aqueous sodium carbonate (saturated). The chloroform layer was dried ($MgSO_4$) and evaporated. The residual mixture of isomers was purified by gradient chromatography on silica gel and eluting with $CHCl_3/EtOAc/MeOH(49/49/2-43/43/14)$ to give essentially pure fractions of high $R_F$ and low $R_F$ isomers.

The higher $R_F$ isomer (1.8 g) was dissolved in ethyl acetate and treated with maleic acid (1.1 eq.). Diethyl ether was added to precipitate a white solid which was dried at 75° C. in vacuo to give (E) -2,8-Dimethyl-1-oxa-8-azaspiro[4.5] decan-3-one oxime methyl ether maleate (1.8 g), mp 146°–147° C.

|  | C | H | N |
|---|---|---|---|
| Theory: | 54.87 | 7.37 | 8.53 |
| Found: | 54.92 | 7.36 | 8.58 |

The lower $R_F$ isomer (0.51 g) was dissolved in ethyl acetate and treated with maleic acid (1.1 eq). The precipitated solid (0.45 g) was collected and combined with a similarly prepared material to give a total of 0.6 g which was dried at 75° C. in vacuo to give (Z)-2,8-Dimethyl-1-oxa-8-azaspiro[4.5]decan-3-one oxime methyl ether maleate, mp 146.5°–149.5° C.

|  | C | H | N |
|---|---|---|---|
| Theory: | 54.87 | 7.37 | 8.53 |
| Found: | 54.24 | 7.26 | 8.46 |

EXAMPLE 29

N-Ethoxycarbonyl-2,8-dimethyl 1-oxa-8-azaspiro[4.5]decan-3-one hydrazone fumarate 2,8-Dimethyl-1-oxa-8-azaspiro[4.5]decan-3-one (3 g, 0.017 mol) and ethyl carbazate (1.56 g) were dissolved in absolute EtOH (175 mL) and acidified with HCl/EtOH to pH4. The reaction was stirred overnight at room temperature and then the ethanol was evaporated. The residue was dissolved in $CHCl_3$ and partitioned with aqueous $Na_2CO_3$. The chloroform layer was dried ($Na_2SO_4$) and concentrated. The residue was purified by chromatography on silica gel and eluting with ammoniated 2–10% $MeOH/CHCl_3$ to give 1.4 g of an oil. The oil was dissolved in diethyl ether and acidified with a solution of fumaric acid in diethyl ether. The precipitated solid was recrystallized from ethanol/diethyl ether to give a hygroscopic solid which was dried under high vacuum at 50° C. to give the title compound as a solid mp 103.5°–104.5° C.

|  | C | H | N |
|---|---|---|---|
| Theory: | 52.98 | 7.06 | 10.90 |
| Found: | 52.34 | 7.32 | 11.29 |

EXAMPLE 30

2,8-Dimethyl-1-oxa-8-azaspiro[4.5]decan-3-one 0-[(dimethylamino)carbonyl]oxime fumarate A solution of 2,8-Dimethyl-1-oxa-8-azaspiro [4.5]decan-3-one oxime (1 g, 5 mmol) dissolved in dry THF containing sodium hydride (0.24 g of a 60% oil suspension) was stirred until hydrogen evolution had ceased. (Dimethylamino)carbonyl chloride (0.66 mL) was added and the reaction was stirred at room temperature overnight, then it was heated at reflux for 5 hours. The reaction was treated with aliquots of (dimethylamino)carbonyl chloride and further heating until the reaction was complete. The solvent was evaporated and the residue was dissolved in chloroform, partitioned with aqueous sodium carbonate and the chloroform layer was concentrated to dryness. The residue was chromatographed on silica gel and eluted with ammoniated 2–10% $MeOH/CHCl_3$ to give an oil (1 g). The oil was treated with maleic acid (0.43 g) in ethyl acetate and concentrated to dryness. The residue was dissolved in isopropanol/ethylacetate and concentrated under vacuum until turbidity occurred. A small quantity of oil separated and the supernatant solution was decanted and concentrated. The free base was recovered from the maleate salt by treatment with aqueous sodium carbonate and further purified by chromatography. The recovered base (0.3 g) was then treated with fumaric acid in ethylacetate/diethyl ether to give the fumarate salt of the title compound, 0.24 g, mp. 165°–169° C.

|  | C | H | N |
|---|---|---|---|
| Theory: | 52.98 | 7.06 | 10.90 |
| Found: | 52.89 | 7.01 | 10.50 |

We claim:
1. A compound of formula I,

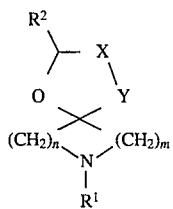

wherein $R^1$ represents hydrogen or alkyl $C_{1-3}$, $R^2$ represents hydrogen, alkyl $C_{1-6}$, alkenyl $C_{3-6}$ or alkynyl $C_{3-6}$, n and m are integers from 1 to 3, provided that n+m=4, and one of X and Y represents $CH_2$ and the other represents $CHR^3$, $C=CHR^4$ or $C=NR^5$, in which $R^3$ represents $NR^6R^7$, $NR^8R^9$, $CO_2R^{10}$, 3-methyl-1,2,4-oxadiazol-5-yl, or 3-amino-1,2,4-oxadiazol-5-yl, $R^4$ represents alkanoyl $C_{1-6}$ or $COOR^{11}$, $R^5$ represents $OR^{12}$, alkanoyloxy $C_{1-6}$, benzoyloxy, $C_{1-6}$ alkanoylamino, $OCONR^{13}R^{14}$, $NHCONR^{15}R^{16}$ or $NHCOOR^{17}$, $R^6$ represents $C_{1-6}$ alkanoyl or $C_{1-6}$ alkoxycarbonyl, and $R^7$, $R^8$, $R^9$, $R^{10}$, $R^{11}$, $R^{13}$, $R^{14}$, $R^{15}$, $R^{16}$ and $R^{17}$ represent hydrogen or $C_{1-6}$ alkyl, and $R^{12}$ represents hydrogen, $C_{1-6}$ alkyl, $C_{3-6}$ alkenyl or $C_{3-6}$ alkynyl, and salts and solvates thereof.

2. A compound according to claim 1, wherein Y represents $CH_2$.

3. A compound according to claim 1, wherein $R^2$ represents methyl.

4. A compound according to claim 1, wherein $R^1$ represents methyl.

5. A compound according to claim 1, wherein $R^2$ represents methyl, n and m both represent 2, and Y represents $CH_2$.

6. A compound according to claim 1, which is

8-Methyl-1-oxa-8-azaspiro[4.5]decan-3-one oxime,

8-Methyl-1-oxa-8-azaspiro[4.5]decan-3-one oxime methyl ether,

8-Methyl-1-oxa-8-azaspiro[4.5]decan-3-one O-acetyloxime, 8-methyl-1-oxa-8-azaspiro[4.5]decan-3-one O-propionyloxime, 8-Methyl-1-oxa-8-azaspiro[4.5]decan-3-one-O-benzoyloxime, 2,8-Dimethyl-1-oxa-8-azaspiro[4.5]decan-3-one O-propionyloxime, 2,8-Dimethyl-1-oxa-8-azaspiro[4.5]decan-3-one oxime, 3-Amino-8-methyl-1-oxa-8-azaspiro[4.5]decane, 3-Amino-2,8-dimethyl-1-oxa-8-azaspiro[4.5]decane, (E)-Methyl 2-[2,8-dimethyl-1-oxa-8-azaspiro[4.5]-decan-3-ylidine]acetate, (Z)-Methyl 2-[2,8-dimethyl-1-oxa-8-azaspior[4.5]-decan-3-ylidine]acetate, Methyl 2-[8-methyl-1-oxa-8-azaspiro[4.5]decan-3-ylidine]acetate, Methyl 2,8-dimethyl-1-oxa-8-azaspiro[4.5]decane-3-carboxylate, 2,8-Dimethyl-3-(3-methyl-1,2,4-oxadiazol-5-yl)-1-oxa-8-azaspiro[4.5]decane, 3-Acetamido-2,8-dimethyl-1-oxa-8-azaspiro[4.5]-decane, 2,8-Dimethyl-3-(dimethylamino)-1-oxa-8-azaspiro[4.5]-decane, (2,8-Dimethyl-1-oxa-8-azaspiro[4.5]decan-3-yl) carbamic acid ethyl ester, N-Acetyl-2,8-dimethyl-1-oxa-8-azaspiro[4.5]decan-3-one hydrazone, 2,8-Dimethyl-1-oxa-8-azaspiro[4.5]decan-3-one semicarbazone, (E)-2,8-Dimethyl-1-oxa-8-azaspiro[4.5]decan-3-one oxime methyl ether, (Z)-2,8-Dimethyl-1-oxa-8-azaspiro[4.5]decan-3-one oxime methyl ether, N-Ethoxycarbonyl-2,8-dimethyl 1-oxa-8-azaspiro[4.5]decan-3-one hydrazone, 2,8-Dimethyl-1-oxa-8-azaspiro[4.5]decan-3-one O-[(dimethylamino)carbonyl]oxime fumarate, or a salt or solvate of any one thereof.

7. A compound according to claim 1 in the form of an acid addition salt.

8. A method for the treatment of pain comprising administering to a patient suffering from pain an analgesic effective amount of one or more compounds of formula (I) as defined in claim 1.

9. A pharmaceutical composition comprising a compound of formula I, as defined in claim 1, in admixture with a pharmaceutically acceptable carrier.